(12) United States Patent
Chen et al.

(10) Patent No.: US 9,986,973 B2
(45) Date of Patent: Jun. 5, 2018

(54) METHOD FOR SHEAR WAVE ULTRASOUND VIBROMETRY WITH INTERLEAVED PUSH AND DETECTION PULSES

(75) Inventors: Shigao Chen, Rochester, MN (US); James F. Greenleaf, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 1636 days.

(21) Appl. No.: 13/092,574

(22) Filed: Apr. 22, 2011

(65) Prior Publication Data

US 2011/0263978 A1 Oct. 27, 2011

Related U.S. Application Data

(60) Provisional application No. 61/327,539, filed on Apr. 23, 2010.

(51) Int. Cl.
*A61B 8/00* (2006.01)
*A61B 8/08* (2006.01)
*G01S 7/52* (2006.01)

(52) U.S. Cl.
CPC .............. *A61B 8/48* (2013.01); *A61B 8/485* (2013.01); *G01S 7/52022* (2013.01); *G01S 7/52042* (2013.01)

(58) Field of Classification Search
USPC ........................................ 600/438, 407, 437
See application file for complete search history.

(56) References Cited

U.S. PATENT DOCUMENTS

| 7,753,847 B2 | 7/2010 | Greenleaf et al. |
| 7,785,259 B2 | 8/2010 | Zheng et al. |
| 2006/0052699 A1* | 3/2006 | Angelsen et al. ............. 600/437 |
| 2008/0249408 A1* | 10/2008 | Palmeri et al. ............... 600/438 |

OTHER PUBLICATIONS

Shearwave Dispersion Ultrasound Vibrometry (SDUV) for Measuring Tissue Elasticity and Viscosity; Chen et al; Pupblished in final form as: IEEE Trans Ultrason Ferroelectr Freq Control. Jan. 2009; 56(1): 55-62. doi:10.1109/TUFFC. 2009.1005.*

(Continued)

*Primary Examiner* — Joel F Brutus
(74) *Attorney, Agent, or Firm* — Jonathan D. Stone

(57) ABSTRACT

A shear wave dispersion ultrasound vibrometry ("SDUV") method for measuring a mechanical property of a subject is provided. Particularly, a set of ultrasonic vibration tone bursts is applied to a vibration origin in the subject so that harmonic vibratory motion is imparted to a tissue of interest. The set of vibration tone bursts effectively act like a single vibration pulse that imparts vibratory motion at larger amplitudes than achievable with a single pulse. Multiple ultrasonic detection pulses are then applied to two or more locations in the tissue of interest in order to measure shear waves propagating outward from the vibration origin. From these measurements, phase or amplitude information related to the shear wave propagation is determined and used to calculate a shear wave speed. Using the shear wave speed information, mechanical properties of the tissue are calculated.

20 Claims, 9 Drawing Sheets

(56) References Cited

OTHER PUBLICATIONS

Chen et al, Complex Stiffness Quantification Using Ultrasound Stimulated Vibrometry, IEEE Ultrasonics Symposium 2003; pp. 941-944.
Hasegawa et al, Improving Accuracy in Estimation of Artery-Wall Displacement by Referring to Center Frequency of RF Echo, IEEE Trans. Ultrason., Ferroelec., Freq. Contr., 2006; 53(1):52-63.
Jensen et al, "Calculation of Pressure Fields from Arbitrarily Shaped, Apodized, and Excited Ultrasound Transcucers," IEEE Trans. Ultrason., Ferroelec., Freq. Contr., 1992, 39(2):262-267.
Jensen, "Field: A Program for Simulating Ultrasound Systems," Paper presented at the 10th Nordic-Baltic Conference on Biomedical Imaging Published in Medical & Biological Engineering & Computing, pp. 351-353, vol. 34, Supplement 1, Part 1, 1996.
Nightingale, et al., On the Feasibility of Remote Palpation Suing Acoustic Radiation Force, J. Accoust. Soc. Am., 2001, 110(1):625-634.

\* cited by examiner

METHOD FOR SHEAR WAVE ULTRASOUND VIBROMETRY WITH INTERLEAVED PUSH AND DETECTION PULSES

CROSS-REFERENCE TO RELATED APPLICATIONS

This application claims the benefit of U.S. Provisional Patent Application Ser. No. 61/327,539, filed on Apr. 23, 2010, and entitled "Method for Shearwave Ultrasound Vibrometry with Interleaved Push and Detection Pulses."

STATEMENT REGARDING FEDERALLY SPONSORED RESEARCH

This invention was made with government support under DK082408 awarded by the National Institutes of Health. The government has certain rights in the invention.

BACKGROUND OF THE INVENTION

The field of the invention is coherent imaging using vibratory energy, such as ultrasound, and, in particular, systems and methods for shear wave dispersion ultrasound vibrometry ("SDUV").

There are a number of modes in which ultrasound can be used to produce images of objects. For example, an ultrasound transmitter may be placed on one side of the object and sound transmitted through the object to an ultrasound receiver placed on the other side of the object. With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("reflection," "backscatter," or "echo" mode).

There are a number of well known backscatter methods for acquiring ultrasound data. In the so-called "A-mode" method, an ultrasound pulse is directed into the object by an ultrasound transducer and the amplitude of the reflected sound is recorded over a period of time. The amplitude of the echo signal is proportional to the scattering strength of the reflectors in the object and the time delay is proportional to the range of the reflectors from the transducer. In the so-called "B-mode" method, the transducer transmits a series of ultrasonic pulses as it is scanned across the object along a single axis of motion. The resulting echo signals are recorded as with the A-mode method and their amplitude is used to modulate the brightness of pixels on a display. The location of the transducer and the time delay of the received echo signals locates the pixels to be illuminated. With the B-mode method, enough data are acquired from which a two-dimensional image of the reflectors can be reconstructed. Rather than physically moving the transducer over the subject to perform a scan it is more common to employ an array of transducer elements and electronically move an ultrasonic beam over a region in the subject.

The ultrasound transducer typically has a number of piezoelectric elements arranged in an array and driven with separate voltages. By controlling the time delay, or phase, and amplitude of the applied voltages, the ultrasonic waves produced by the piezoelectric elements ("transmission mode") combine to produce a net ultrasonic wave focused at a selected point. By controlling the time delay and amplitude of the applied voltages, this focal point can be moved in a plane to scan the subject.

The same principles apply when the transducer is employed to receive the reflected sound ("receiver mode"). That is, the voltages produced at the transducer elements in the array are summed together such that the net signal is indicative of the sound reflected from a single focal point in the subject. As with the transmission mode, this focused reception of the ultrasonic energy is achieved by imparting separate time delays, or phase shifts, and gains to the echo signal received by each transducer array element.

There are a number of electronic methods for performing a scan using a transducer having an array of separately operable elements. These methods include linear array systems and phased array systems.

A linear array system includes a transducer having a large number of elements disposed in a line. A small group of elements are energized to produce an ultrasonic beam that travels away from the transducer, perpendicular to its surface. The group of energized elements is translated along the length of the transducer during the scan to produce a corresponding series of beams that produce echo signals from a two-dimensional region in the subject. To focus each beam that is produced, the pulsing of the inner elements in each energized group is delayed with respect to the pulsing of the outer elements. The time delays determine the depth of focus which can be changed during scanning. The same delay factors are applied when receiving the echo signals to provide dynamic focusing during the receive mode.

A phased array system commonly employs so-called phased array sector scanning ("PASS"). Such a scan is comprised of a series of measurements in which all of the elements of a transducer array are used to transmit a steered ultrasonic beam. The system then switches to receive mode after a short time interval, and the reflected ultrasonic wave is received by all of the transducer elements. Typically, the transmission and reception are steered in the same direction, θ, during each measurement to acquire data from a series of points along a scan line. The receiver is dynamically focused at a succession of ranges, R, along the scan line as the reflected ultrasonic waves are received. A series of measurements are made at successive steering angles, θ, to scan a pie-shaped sector of the subject. The time required to conduct the entire scan is a function of the time required to make each measurement and the number of measurements required to cover the entire region of interest at the desired resolution and signal-to-noise ratio. For example, a total of 128 scan lines may be acquired over a sector spanning 90 degrees, with each scan line being steered in increments of 0.70 degrees.

The same scanning methods may be used to acquire a three-dimensional image of the subject. The transducer in such case is a two-dimensional array of elements which steer a beam throughout a volume of interest or linearly scan a plurality of adjacent two-dimensional slices.

Characterization of tissue mechanical properties, particularly the elasticity or tactile hardness of tissue, has important medical applications because these properties are closely linked to tissue state with respect to pathology. For example, breast cancers are often first detected by the palpation of lesions with abnormal hardness. In another example, a measurement of liver stiffness can been used as a non-invasive alternative for liver fibrosis staging.

Recently, an ultrasound technique for measuring mechanical properties of tissues, such as stiffness and viscosity, called shear wave dispersion ultrasound vibrometry ("SDUV") was developed. This SDUV technique is described, for example, in U.S. Pat. Nos. 7,785,259, and 7,753,847, which are herein incorporated by reference in their entirety. A focused ultrasound beam, operating within FDA safety limits, is applied to a subject to generate harmonic shear waves in a tissue of interest. The propagation speed of the induced shear wave is frequency dependent, or "dispersive," and relates to the mechanical properties of the tissue of interest. Shear wave speeds at a number of frequencies are measured by pulse echo ultrasound and subsequently fit with a theoretical dispersion model to inversely solve for tissue elasticity and viscosity. These shear wave speeds are estimated from the phase of tissue vibration that is detected between two or more points with known distance along the shear wave propagation path.

One feature of the SDUV method is the use of a so-called "binary pushing pulse" that allows the operation of one single array ultrasound transducer for both motion excitation and the echo signal detection. For example, the transducer focuses ultrasound at one location, the "vibration origin," to vibrate the tissue of interest and then electronically steers its focus to another location, a "motion detection point," for echo signal vibration detection. Instead of continuously vibrating the tissue of interest, the "pushing" ultrasound is turned on during a vibration time period to vibrate the tissue and turned off to provide a time window for the pulse echo motion detection. When the pushing pulse is off, a series of short ultrasound pulses is transmitted to the motion detection locations and a corresponding series of echo signals is received and processed to determine the tissue vibration. This intermittent pulse sequencing strategy allows both the production of a shear wave and the monitoring of its propagation at the same time with a single array transducer.

A technical challenge for the SDUV method, however, is that the shear wave generated by the pushing ultrasound is small and difficult to detect with pulse echo ultrasound. For human applications, the intensity of an ultrasound push beam is limited by the FDA, such that the mechanical index ("MI") should be lower than 1.9. In practice, MI is targeted to be at a lower value, such as around 1.4, to ensure that variations among different ultrasound scanners will never generate an MI that exceeds 1.9. This is important for practice because calibrating every ultrasound scanner to ensure MI is less than 1.9 is cost prohibitive, and requires a burdensome amount of time for a complete calibration. The result of using lower MI, however, is that vibratory tissue motion, which increases dramatically with MI, is too small, thereby making detection unreliable. The push beam duration can be extended to increase tissue motion; however, a push beam that is too long will interfere with subsequent detection pulses. By way of example, and referring to FIG. 1, long push pulses interfere with and corrupt two subsequent detection beams, leading to two missing data points in SDUV analysis. Missing data points that are recovered by interpolation introduce errors in the estimation of shear wave speeds at higher frequencies. The time interval between subsequent detection beams, termed the pulse repetition period, cannot be readily increased to avoid interference because the pulse repetition frequency, which is the inverse of pulse repetition period, for detect beams, $PRF_D$, should be sufficiently high to detect shear waves at higher harmonics.

It would therefore be desirable to provide a method for shear wave dispersion ultrasound vibrometry ("SDUV") that imparts vibratory motion to a tissue of interest with larger amplitudes than achievable with currently available techniques, but does so in a manner that does not significantly impede the ability to detect shear wave propagation and that remains within FDA safety limits for mechanical index.

SUMMARY OF THE INVENTION

The present invention overcomes the aforementioned drawbacks by providing a method for shear wave dispersion ultrasound vibrometry ("SDUV"), in which a single push pulse is replaced with a set of shorter push tone bursts, such that vibratory motions with larger amplitudes are imparted to a tissue of interest without exceeding FDA safety limits for mechanical index. Moreover, the detection of the induced propagating shear waves is not significantly impeded because the detection pulse repetition frequency does not need to be reduced when using a set of push tone bursts in lieu of a single push pulse of longer duration.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
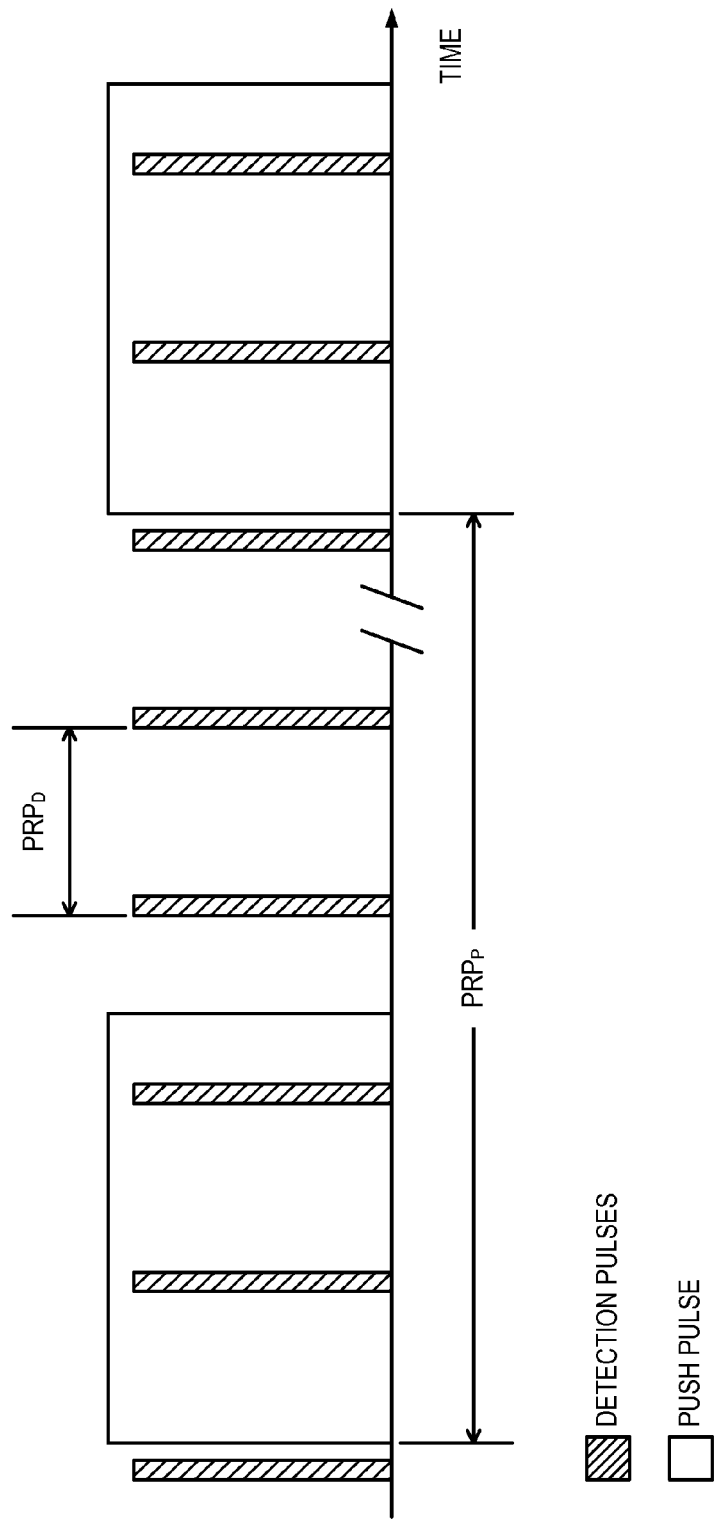
FIG. 1 is a pulse timing diagram indicating the application of ultrasonic vibration and detection pulses, in which an ultrasonic vibration pulse having a significantly long duration is shown.

Shear wave dispersion ultrasound vibrometry ("SDUV") techniques use a long duration (hundreds of microseconds), focused ultrasound beam to generate vibration within a tissue of interest. This vibration, or "push," beam is transmitted at the same push location, or vibration origin, and is repeated at a pulse repetition frequency ("PRF"), denoted $PRF_P$. For example, $PRF_P$ is 100 Hz, in which case vibratory tissue motion is generated in the tissue of interest at a frequency of 100 Hz and higher harmonics, such as 200, 300, and 400 Hz.

As a result of this vibratory motion, shear waves propagate outwards from the vibration origin. These shear waves can be detected at several positions, or motion detection points, along the propagation path of the waves. The detection of the shear waves is achieved by applying a detection ultrasound beam to each motion detection point using a pulse-echo ultrasound mode. The shear wave propagation speed, $c_s$, can be calculated from the phase of the shear wave detected at two or more detection points. Shear wave speeds at the prescribed frequency, for example 100 Hz, and its higher harmonics, such as 200, 300, 400, and 500 Hz, can be measured simultaneously because vibrations generated by a push beam are multi-tone. Shear wave speeds measured at these frequencies can be used with a model, such as the Voigt dispersion model, to estimate tissue stiffness, $\mu_1$, and viscosity, $\mu_2$, as will be described below in detail.

In general, the displacement of a point in a tissue that is in harmonic vibratory motion can be represented in the following form:

$$D(t) = D_0 \sin(\omega_s t + \phi_s) \quad \text{Eqn. (1);}$$

where $D_0$ is an amplitude of the motion displacement, $\omega_s$ is the tissue vibration frequency, and $\phi_s$ is the tissue vibration phase. The velocity of this motion is then of the form:

$$v(t) = \frac{dD(t)}{dt} = v_0 \cos(\omega_s t + \phi_s); \quad \text{Eqn. (2)}$$

where $v_0 = D_0 \omega_s$ is an amplitude of the motion velocity. When a pulse echo ultrasound system is focused on the tissue motion, the motion is represented as oscillatory Doppler shifts in the received echo signals. The received echo signals, therefore, have the form:

$$r(t_f, t_s) = A(t_f, t_s)\cos(\omega_f t_f + \phi_f + \beta \sin(\omega_s t_s + \phi_s)) \quad \text{Eqn. (3);}$$

where $A(t_f, t_s)$ is the amplitude of the complex envelope of the received echo signal; $t_f$ is fast time, which is representative of depth; $t_s$ is slow time, which is representative of pulse repetition; $\omega_f$ is the transmission center frequency; $\omega_s$ is again the tissue vibration frequency; $\phi_s$ is again the tissue vibration phase; and $\theta$ is an angle between the ultrasound beam and direction of tissue motion. The vibration becomes a phase term of the angular modulation. Furthermore, the modulation index, $\beta$, is:

$$\beta = \frac{2 v_0 \omega_f \cos(\theta)}{\omega_s c}; \quad \text{Eqn. (4)}$$

where $c$ is the sound speed in the tissue. Quadrature demodulation of the received echo signals yields in-phase, $I(t_f, t_s)$, and quadrature, $Q(t_f, t_s)$, terms, which have the form:

$$I(t_f, t_s) = A(t_f, t_s)\cos(\beta \sin(\omega_s t_s + \phi_s) + \phi_f + \phi_0) \quad \text{Eqn. (5);}$$

and $$Q(t_f, t_s) = A(t_f, t_s)\sin(\beta \sin(\omega_s t_s + \phi_s) + \phi_f + \phi_0) \quad \text{Eqn. (6);}$$

respectively. Here, $\phi_0$ is a constant phase added during the quadrature demodulation to keep $I(t_f, t_s)$ nonzero; that is, to be either all positive, or all negative, in slow time at a location. In the end, this constant phase term is removed, as shown below. The arc tangent of the ratio between $Q(t_f, t_s)$ and $I(t_f, t_s)$ is calculated accordingly:

$$s(t_f, t_s) = -\tan^{-1}\left(\frac{Q(t_f, t_s)}{I(t_f, t_s)}\right); \quad \text{Eqn. (7)}$$

and $$y(t_s) = s(t_f, t_s) - \bar{s}(t_f, t_s) = \beta \sin(\omega_s t_s + \phi_s) \quad \text{Eqn. (8);}$$

where $\bar{s}(t_f, t_s)$ is a mean value of $s(t_f, t_s)$ in slow time. If the sampling frequency in fast time is high, $I(t_f, t_s)$ and $Q(t_f, t_s)$ can be averaged with a limited length in fast time to reduce noise before $s(t_f, t_s)$ is calculated. A band-pass filter ("BPF") centered at the vibration frequency can improve $y(t_s)$ by reducing noise and distortions. The amplitude, $\beta$, of the oscillatory Doppler shifts can be directly estimated from $y(t_s)$ by:

$$\beta = \sqrt{2}\sigma_y \quad \text{Eqn. (9);}$$

where $\sigma_y$ is a standard deviation of $y(t_s)$. However, the phase and amplitude of the Doppler shifts in Eqn. (8) can also be directly obtained by another quadrature demodulation, at the vibration frequency, in the direction of the slow time, which yields:

$$I(t_s) = \beta \cos(\phi_s) \quad \text{Eqn. (10);}$$

and $$Q(t_s) = \beta \sin(\phi_s) \quad \text{Eqn. (11).}$$

As a result of this demodulation, the amplitude can be obtained by:

$$\beta(t_s) = \sqrt{I(t_s)^2 + Q(t_s)^2} \quad \text{Eqn. (12);}$$

and the phase by:

$$\phi_s(t_s) = \tan^{-1}\left(\frac{Q(t_s)}{I(t_s)}\right). \quad \text{Eqn. (13)}$$

The amplitude of the oscillatory Doppler shifts can also be directly measured by applying a turbulence estimation method to the received echo signals, $r(t_f, t_s)$, to estimate the variance of motion velocity.

In practice, the data acquired with the ultrasound system is noisy and stochastic in nature. Therefore, a Kalman filter process is employed to recursively estimate the phase and amplitude of the harmonic shear wave motion. As described, for example, by R. G. Brown and P. Y. C. Hwang in *Introduction To Random Signals and Applied Kalman Filtering*, 3rd Edition, John Wily & Sons, 1997, a Kalman filter is a numerical method used to track a time-varying signal in the presence of noise. If the signal can be characterized by some number of parameters that vary slowly with time, then Kalman filtering can be used to tell how incoming raw measurements should be processed to best estimate those parameters as a function of time. In this application, a Kalman filter extracts information about the imparted harmonic motion from random and noisy measurement data with known vibration frequency and unknown vibration amplitude and phase.

Figure 2:
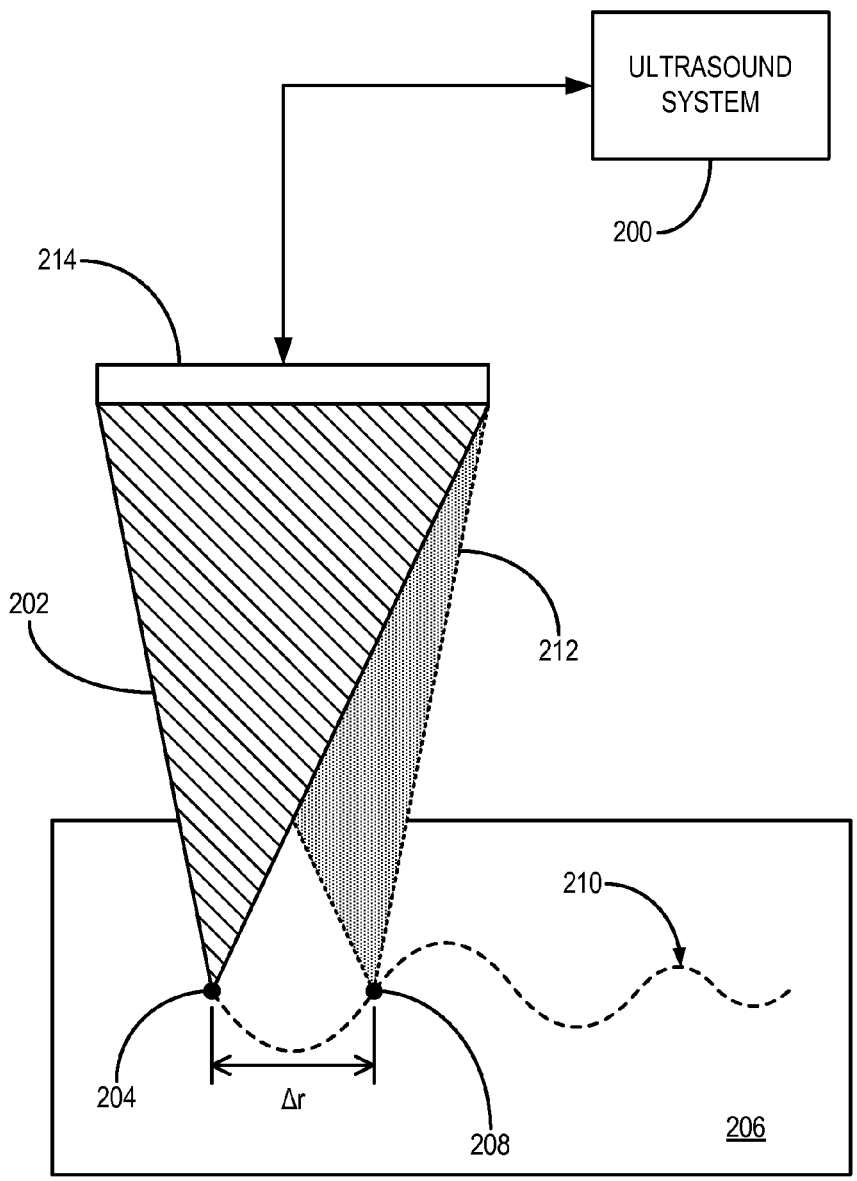
FIG. 2 is a block diagram of a shear wave dispersion ultrasound vibrometry ("SDUV") system that employs the present invention.

By way of example, and referring initially to FIG. 2, an ultrasonic vibration pulse 202, or "pushing pulse," is applied to a vibration origin 204 in a tissue of interest 206 in order to induce vibratory motion 210 in the tissue 206. This vibratory motion 210 at a location in the tissue is interrogated by applying a series of ultrasonic detection pulses 212 to one or more motion detection points 208. Tissue vibration obtained from the $k^{th}$ ultrasound echo has the form:

$$y_k = [\sin(\omega_s kT) \; \cos(\omega_s kT)] \begin{bmatrix} \beta\cos(\phi_s) \\ \beta\sin(\phi_s) \end{bmatrix} + n_k; \quad \text{Eqn. (14)}$$

where $\omega_s$ is the frequency of the tissue vibration; T is the pulse repetition period ("PRP") between application of ultrasonic vibration pulses, which is equal to the inverse of the pulse repetition frequency ("PRF"), or 1/PRF; $\beta$ and $\phi_s$ are the vibration amplitude and phase to be estimated, respectively; and $n_k$ is a white noise sequence having a variance, R. Eqn. (14) can be rewritten as:

$$y_k = H_k x_k + n_k \quad \text{Eqn. (15);}$$

where $H_k$ is a measurement vector having the form:

$$H_k = [\sin(\omega_s kT)\cos(\omega_s kT)] \quad \text{Eqn. (16);}$$

and $x_k$ is a state variable having the form:

$$x_k = \begin{bmatrix} \beta\cos(\phi_s) \\ \beta\sin(\phi_s) \end{bmatrix}; \quad \text{Eqn. (17)}$$

In this form, the corresponding state equation is:

$$x_k = \Phi x_{k-1} + w_k \quad \text{Eqn. (18);}$$

where $w_k$ is a white driving sequence vector that allows some variations in the vibration amplitude and phase, and $\Phi$ is a transition matrix, which has the form:

$$\Phi = \begin{bmatrix} 1 & 0 \\ 0 & 1 \end{bmatrix}. \quad \text{Eqn. (19)}$$

When the ultrasonic detection pulses are transmitted at a fixed time interval T, Eqns. (15)-(18) are updated at the same rate, T, in the Kalman filter. As is described, for example, in U.S. Pat. No. 7,753,847, which is herein incorporated by reference in its entirety, the Kalman filter is recursively applied to extract, from the noisy echo signals, the amplitude and phase of the underlying signal indicative of the harmonic shear wave motion. In such a manner, the amplitude and phase parameters have the form:

$$\beta = \sqrt{x_k[1]^2 + x_k[2]^2} \quad \text{Eqn. (20);}$$

$$\phi_s = a\tan^{-1}\left(\frac{x_k[2]}{x_k[1]}\right); \quad \text{Eqn. (21)}$$

where $x_k[1] = \beta \cos(\phi_s)$ and $x_k[2] = \beta \sin(\phi_s)$, as illustrated in Eqn. (17). The above method can be applied to estimate the phase, $\phi_s$, of tissue vibration propagating over a known distance, $\Delta r$. As a result, the shear wave speed can be estimated using the phase change, $\Delta\phi_s$, that occurs over the distance, $\Delta r$, by:

$$c_s = \frac{\omega_s \Delta r}{\Delta \phi_s}; \quad \text{Eqn. (22)}$$

which is further used to characterize elasticity and viscosity of the tissues, as will be described below.

Thus, in general, SDUV methods use an ultrasonic imaging system to interrogate a tissue of interest with a pulsed ultrasound beam and to examine the resulting echo signals in order to measure the phase and amplitude of the vibratory motion imparted to the tissue of interest. The challenge is to extract this information from the echo signals from vibratory motion having amplitudes in the submicron-micrometer range. This challenge is made more difficult by the fact that the amount by which the intensity of the push pulses can be increased is limited by FDA safety limits; thus, to increase the amplitude of the vibratory motion, the duration of the push pulse must be increased. However, increasing the duration of the push pulse does not provide an acceptable alternative to increasing the intensity of the push pulse because doing so interferes with the application of the detection pulses.

To address this problem, it has been discovered by the inventors that a sequence of short tone bursts may be utilized to replace a single, long duration push pulse in order to increase the amplitude of vibratory motion induced in a subject while remaining within FDA safety limits of ultrasound intensity. Each tone burst in the push pulse set is shorter than the duration of the push pulses used in previous techniques. For example, each tone burst has a duration of tens of microseconds as compared to the duration of hundreds of milliseconds used in previous techniques. The collective effect of these multiple short tone bursts mimics a long push pulse, thereby generating sufficient vibratory tissue motion for detection by SDUV.

The pulse repetition frequency of these short bone bursts, $PRF_T$, is preferentially identical to the pulse repetition frequency of the detection pulses, $PRF_D$. Put another way, the pulse repetition period, which is the inverse of pulse repetition frequency, between each push tone burst is the same as it is between each detection pulse. While the push pulse has been replaced with a set of push tone bursts, the frequencies of the generated shear waves are still controlled by the pulse repetition frequency of the push pulse sets, $PRF_P$, which is defined the same as the pulse repetition frequency for the original push pulses. An added benefit of using the set of push tone bursts is the ability to achieve higher detection pulse repetition frequency, $PRF_D$, values compared to those achievable with a single, longer duration push pulse. Higher detection pulse repetition frequencies, $PRF_D$, are beneficial for SDUV analysis because with higher $PRF_D$ values, more data points can be collected. Additionally, measurements of motion during collective pushing can be done, thereby allowing estimation of tissue stiffness and viscosity by other techniques, such as by using a creep or recovery curve.

Another benefit of the provided method is that the duration of each push tone burst may be reduced by at least an order of magnitude, thereby minimizing power droop of the ultrasound scanner. It is noted that ultrasound scanners are typically designed to transmit very short pulses of a few microseconds for B-mode imaging. Thus, low-to-mid-end scanners cannot provide enough power to transmit a longer duration push beam and, as a result, the amplitude of the push beam will droop if the push duration is too long. Power droop can lead to small magnitudes of tissue motion and poor SDUV measurements.

For practical considerations, $PRF_D$ is preferably selected so that there is substantially no interference between the short push tone bursts and the detection beams. For example, a $PRF_D$ of 5 kHz provides for 200 microseconds between successive detection beams. If a short push tone burst is inserted at 100 microseconds after the first detection beam, it will lead to a PRF of 10 kHz between interleaved push tone bursts and detection beams. This arrangement provides a maximum push-detection depth of around 75 mm. It is contemplated that a separation in time of about 100 microseconds should be sufficient to avoid interference between adjacent pulses. It is noted that the short push tone burst does not need to be centered in time between two adjacent detection beams. For example, as will be described below, the short push tone burst can be transmitted earlier, such as only 60 microseconds after the first detection beam, thereby allowing more time for the short push tone burst to die out before the next pulse echo detection. It is contemplated that such an arrangement can minimize errors in detection due to interference from the push tone bursts.

Referring again to FIG. 2, an exemplary shear wave dispersion ultrasound vibrometry ("SDUV") system includes an ultrasonic transducer 214 FIG. that is operable to produce focused ultrasound beams. In particular, the transducer 214, such as a linear array transducer, intermittently transmits a beam of ultrasonic vibration pulses 202 to a vibration origin 204 in the tissue of interest 206 to vibrate, or oscillate, the tissue 206 at a prescribed frequency. When the vibration pulses are not being applied to the tissue 204, the focus of the transducer is electronically steered to a motion detection point 208 at a distance, Δr, from the vibration origin 204 and vibratory motion 210 at that point is detected by applying ultrasonic detection pulses 212 thereto. Under the direction of a digital controller of the ultrasound system 200, which controls the transmission and reception of signals, a vibration mode is multiplexed with a detection mode. This enables the detection of the vibratory motion 210 by the same transducer 302 as that transmitting the vibration pulses 202 and both vibration and detection can be achieved without mechanically moving the transducer 214.

Figure 3:
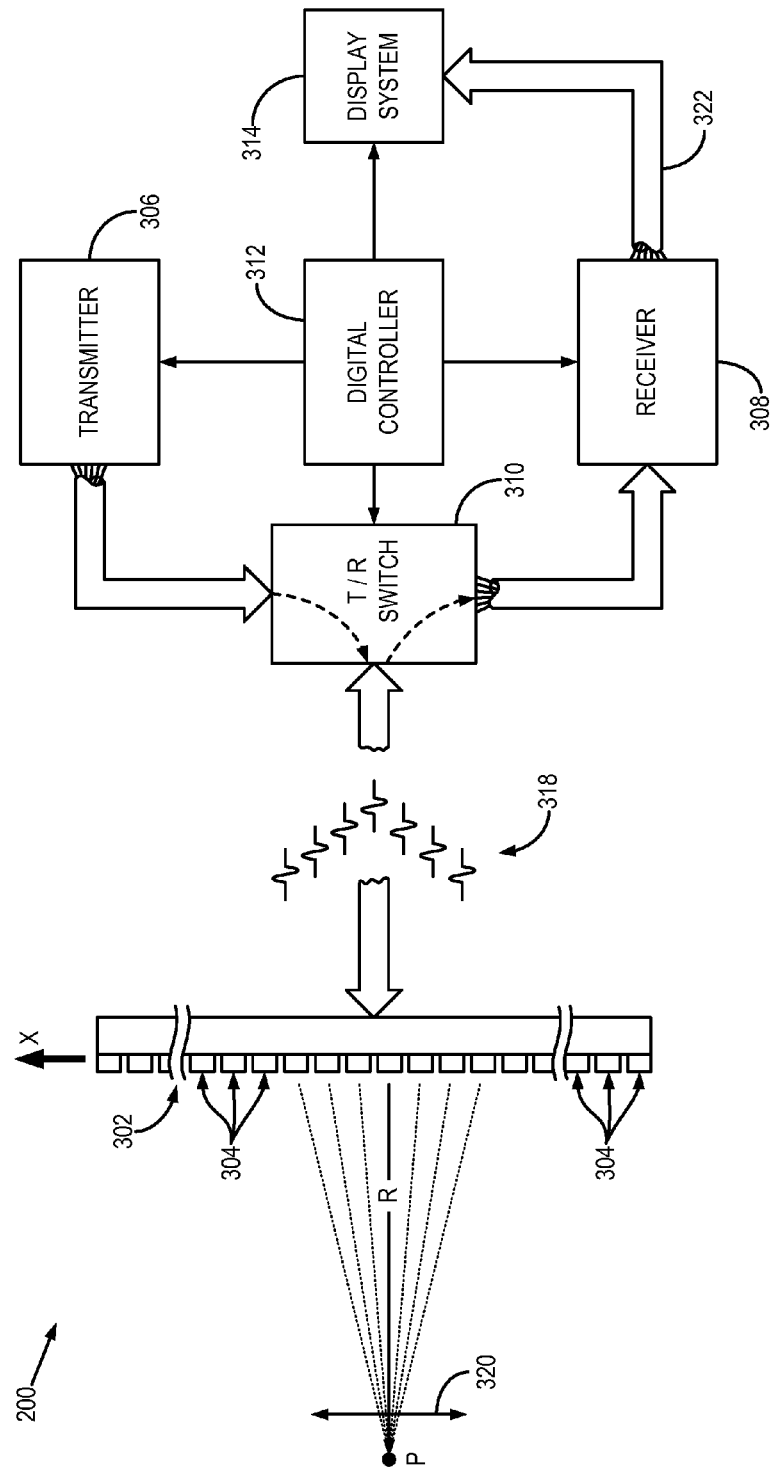
FIG. 3 is a block diagram of an ultrasound system used in the SDUV system of FIG. 2.

Referring particularly now to FIG. 3, an ultrasonic imaging system 200, which forms a part of the SDUV system of FIG. 2, includes a transducer array 302 containing a plurality of separately driven elements 304 that each produce a burst of ultrasonic energy when energized by a pulse produced by a transmitter 306. The ultrasonic energy reflected back to the transducer array 302 from the tissue of interest is converted to an electrical signal by each transducer element 304 and applied separately to a receiver 308 through a set of switches 310. The transmitter 306, receiver 308, and the switches 310 are operated under the control of a digital controller 312 responsive to the commands input by the human operator. A complete scan is performed by acquiring a series of echoes in which the switches 310 are set to their transmit position, the transmitter 306 is gated on momentarily to energize each transducer element 304, the switches 310 are then set to their receive position, and the subsequent echo signals produced by each transducer element 304 are applied to the receiver 308. The separate echo signals from each transducer element 304 are combined in the receiver 308 to produce a single echo signal which is employed to produce a line in an image on a display system 314.

The transmitter 306 drives the transducer array 302 such that an ultrasonic beam is produced which is directed substantially perpendicular to its front surface. To focus this beam at a range, R, from the transducer 302 a subgroup of the elements 304 are energized to produce the beam, and the pulsing of the inner elements 304 in this subgroup are delayed relative to the outer elements 304 as shown at 318. A beam focused at point P results from the interference of the small separate wavelets produced by the subgroup elements. The time delays determine the depth of focus, or range R, and this is typically changed during a scan when a two-dimensional image is to be produced. The same time delay pattern is used when receiving the echo signals resulting in dynamic focusing of the echo signals received by the subgroup of elements 304. In this manner a single scan line in the image is formed.

To generate the next scan line, the subgroup of elements to be energized are shifted one element position along the transducer length and another scan line is required. As indicated by the arrow 320, the focal point, P, of the ultrasonic beam is thus shifted along the length of the transducer 302 by repeatedly shifting the location of the energized subgroup of elements 304.

Figure 4:
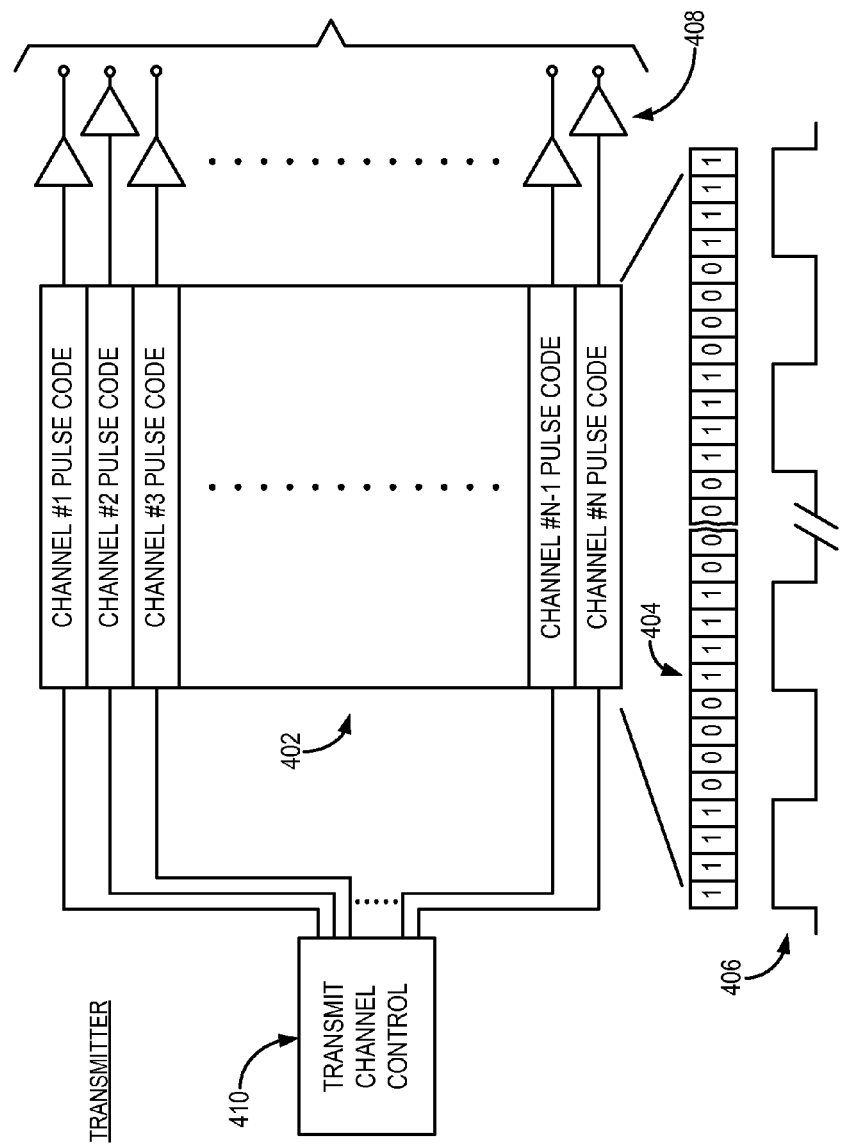
FIG. 4 is a block diagram of a transmitter which forms part of the ultrasound system of FIG. 3.

Referring particularly to FIG. 4, the transmitter 306 includes a set of channel pulse code memories which are indicated collectively at 402. Each pulse code memory 402 stores a bit pattern 404 that determines the frequency of the ultrasonic pulse 406 that is to be produced. This bit pattern is read out of each pulse code memory 402 by a master clock and applied to a driver 408 which amplifies the signal to a power level suitable for driving the transducer 302. In the example shown in FIG. 4, the bit pattern is a sequence of four "1" bits alternated with four "0" bits to produce a 5 megahertz ("MHz") ultrasonic pulse 406. The transducer elements 304 to which these ultrasonic pulses 406 are applied respond by producing ultrasonic energy.

As indicated above, to steer the transmitted beam of the ultrasonic energy in the desired manner, the pulses 406 for each of the N channels must be produced and delayed by the proper amount. These delays are provided by a transmit control 410 which receives control signals from the digital controller 312. When the control signal is received, the transmit control 410 gates a clock signal through to the first transmit channel 402. At each successive delay time interval thereafter, the clock signal is gated through to the next channel pulse code memory 402 until all the channels to be energized are producing their ultrasonic pulses 406. Each transmit channel 402 is reset after its entire bit pattern 404 has been transmitted and the transmitter 306 then waits for the next control signal from the digital controller 312. By operating the transmitter 306 in this manner, ultrasonic energy can be focused on a focal point, P, when practicing the herein described method. This focal point can be steered electronically with the appropriate changes to the timing delays provided by the transmit control 410. The term "focal point," as referred to herein, includes not only a single point object in the usual sense, but also a general region-of-interest to which ultrasound energy is delivered in a substantially focused manner.

Figure 5:
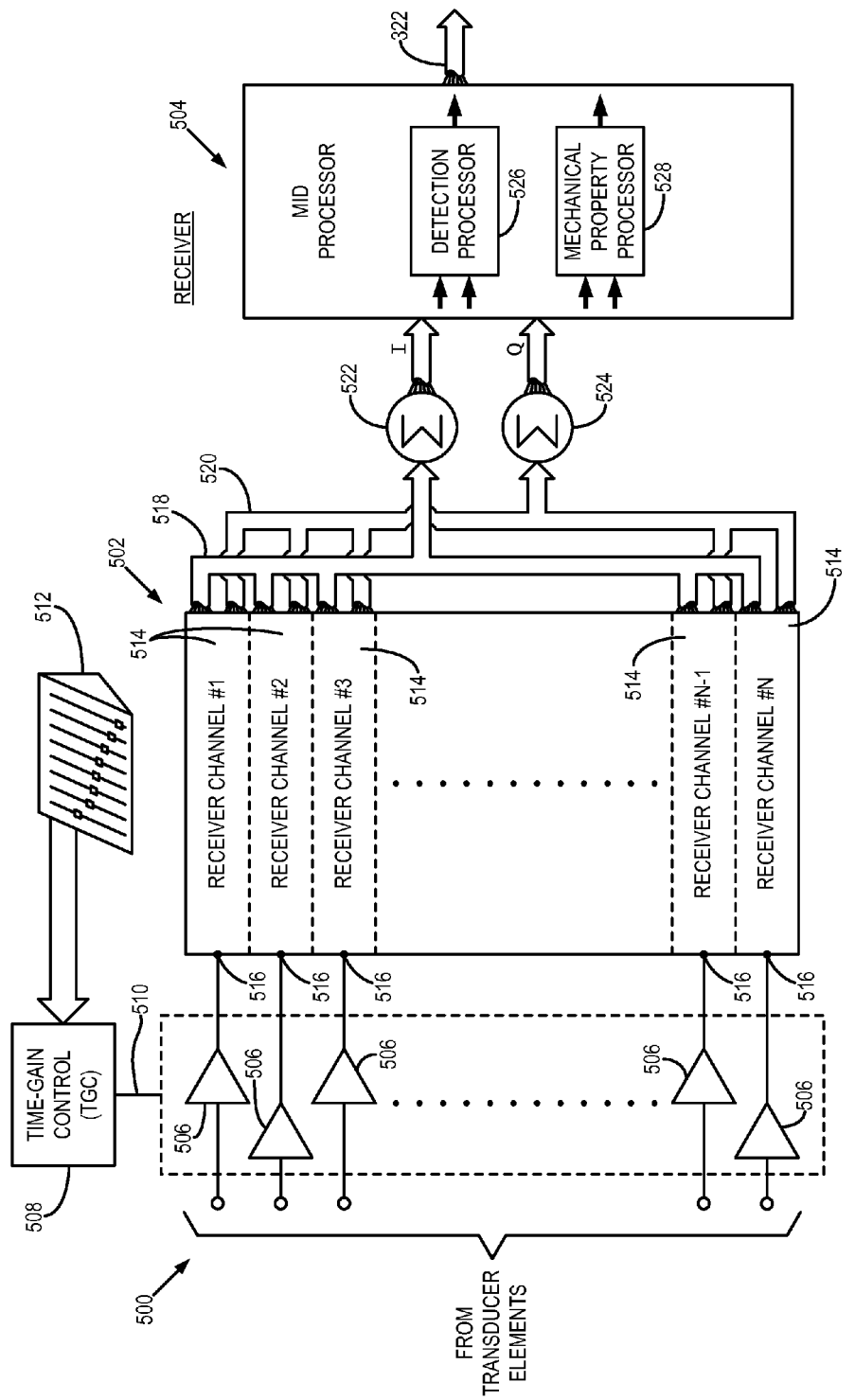
FIG. 5 is a block diagram of a receiver which forms part of the ultrasound system of FIG. 3.

Referring particularly to FIG. 5, the receiver 308 is comprised of three sections: a time-gain control ("TGC") section 500, a beam forming section 502, and a mid processor 504. The time-gain control section 500 includes an amplifier 506 for each of the N receiver channels and a time-gain control circuit 508. The input of each amplifier 506 is connected to a respective one of the transducer elements 304 to receive and amplify the echo signal which it receives. The amount of amplification provided by the amplifiers 506 is controlled through a control line 510 that is driven by the time-gain control circuit 508. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range, R. This amplification is controlled by the operator who manually sets TGC linear potentiometers 512 to values which provide a relatively uniform brightness over the entire range of the scan. The time interval over which the echo signal is acquired determines the range from which it emanates, and this time interval is divided into segments by the TGC control circuit 508. The settings of the potentiometers are employed to set the gain of the amplifiers 506 during each of the respective time intervals so that the echo signal is amplified in ever increasing amounts over the acquisition time interval.

The beam forming section 502 of the receiver 308 includes N separate receiver channels 514. Each receiver channel 514 receives the analog echo signal from one of the TGC amplifiers 506 at an input 516, and it produces a stream of digitized output values on an I bus 518 and a Q bus 520. Each of these I and Q values represents a sample of the echo signal envelope at a specific range, R. These samples have been delayed in the manner described above such that when they are summed at summing points 522 and 524 with the I and Q samples from each of the other receiver channels 514, they indicate the magnitude and phase of the echo signal reflected from a point, P, located at range, R, on the ultrasonic beam.

Referring still to FIG. 5, the mid processor section 504 receives the beam samples from the summing points 522 and 524. The I and Q values of each beam sample is a digital number which represents the in-phase and quadrature components of the magnitude of the reflected sound from a point, P. The mid processor 504 can perform a variety of calculations on these beam samples, where choice is determined by the type of image to be reconstructed. For example, if a conventional magnitude image is to be produced, a detection processor indicated at 526 is implemented in which a digital magnitude, M, is calculated from each beam sample according to:

$$M=\sqrt{I^2+Q^2} \qquad \text{Eqn. (23);}$$

and output at 322 (FIGS. 3 and 5).

The detection processor 526 may also implement correction methods that, for example, examine the received beam samples and calculate corrective values that can be used in subsequent measurements by the transmitter 306 and receiver 308 to improve beam focusing and steering. Such corrections are necessary, for example, to account for the non-homogeneity of the media through which the sound from each transducer element travels during a scan.

The present invention is implemented in part by a mechanical property processor 528 that forms part of the mid-processor 502. As will be explained in detail below, this processor 528 receives the I and Q beam samples acquired during a sequence of measurements of the subject tissue 206 and calculates a mechanical property of the tissue 206.

In order to increase the amplitude of the vibratory motion imparted to the tissue of interest while not exceeding FDA safety limits, a set of ultrasonic vibration tone bursts replace the use of a single ultrasonic vibration pulse. By way of example, exemplary implementations of this approach are illustrated in FIGS. 6-8, as described below.

In general, the following exemplary parameters are employed. The duration of each ultrasonic vibration tone burst in the set may be set to a duration of 20 microseconds, and each tone burst may be applied at a pulse repetition frequency, $PRF_T$, of 4 kHz. Thus, the pulse repetition frequency of the detection pulses, $PRF_D$, may also be preferably set to 4 kHz. Each set of vibration tone bursts may include twenty such tone bursts, although only 4 are shown in FIGS. 6-8 for the purpose of clarity. In addition, the sets of ultrasonic vibration tone bursts may be repeated with a pulse repetition frequency, $PRF_P$, of 100 Hz. It will be readily appreciated by those skilled in the art that these foregoing parameters are exemplary and not limiting. Many other variations of these parameters can be readily implemented.

Figure 6:
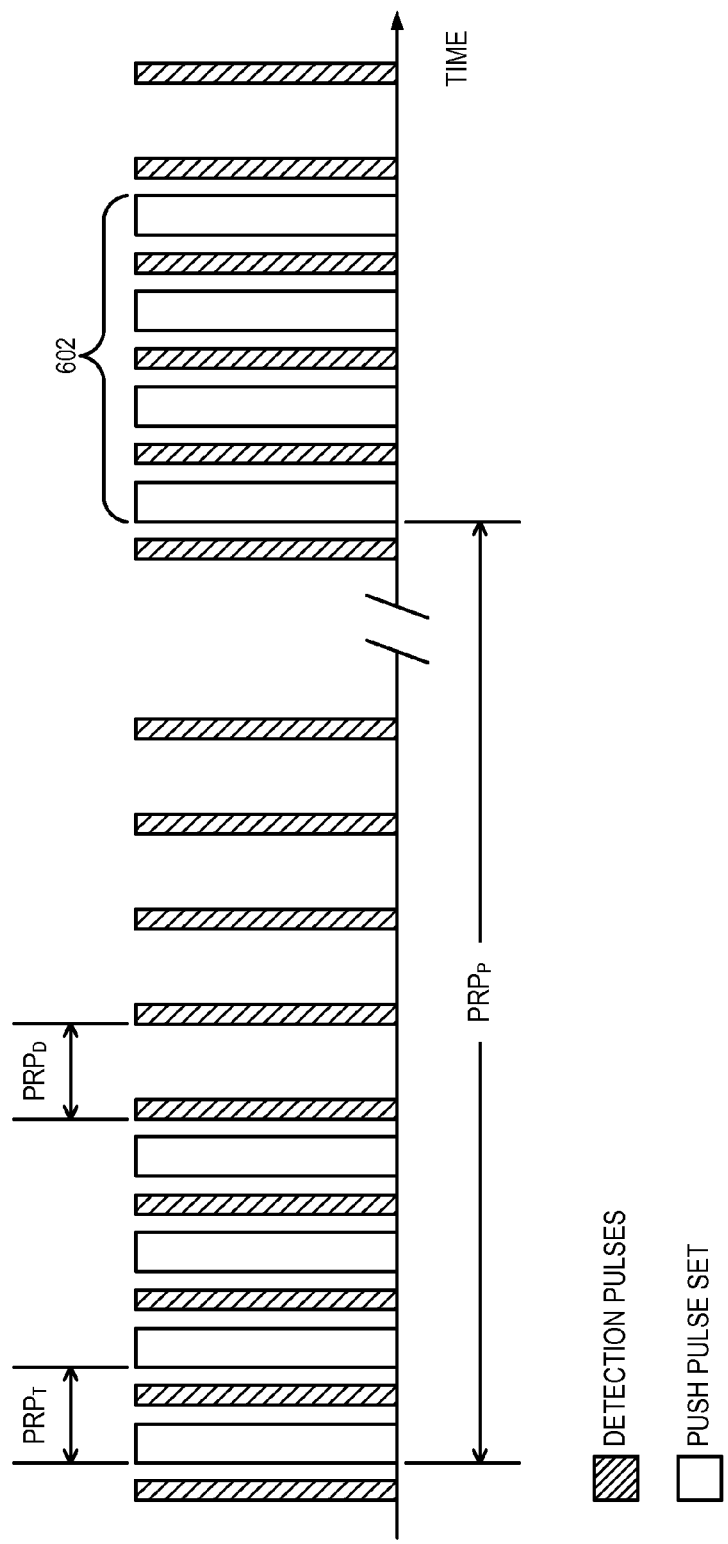
FIG. 6 is a pulse timing diagram indicating the application of a set of short ultrasonic vibration tone bursts and ultrasonic detection pulses in accordance with the present invention.

Referring to FIG. 6, an exemplary temporal pulse sequence in which a set of ultrasonic vibration pulses is interleaved with a series of motion detection pulses is shown. This timing sequence is useful for parallel detection of tissue motions at multiple locations with a single transmission. In general, the propagating shear wave motion can be detected at multiple locations simultaneously using this timing sequence. That is, the pulse echo of each detection pulse is operating in a parallel detection mode. Alternatively in this approach, each detection pulse is focused to detect motion at only one location; therefore, N detect pulses are used to monitor motion at N locations. The detect pulses are steered electronically by the transducer to monitor motion one point at a time in a sequential manner.

Figure 7:
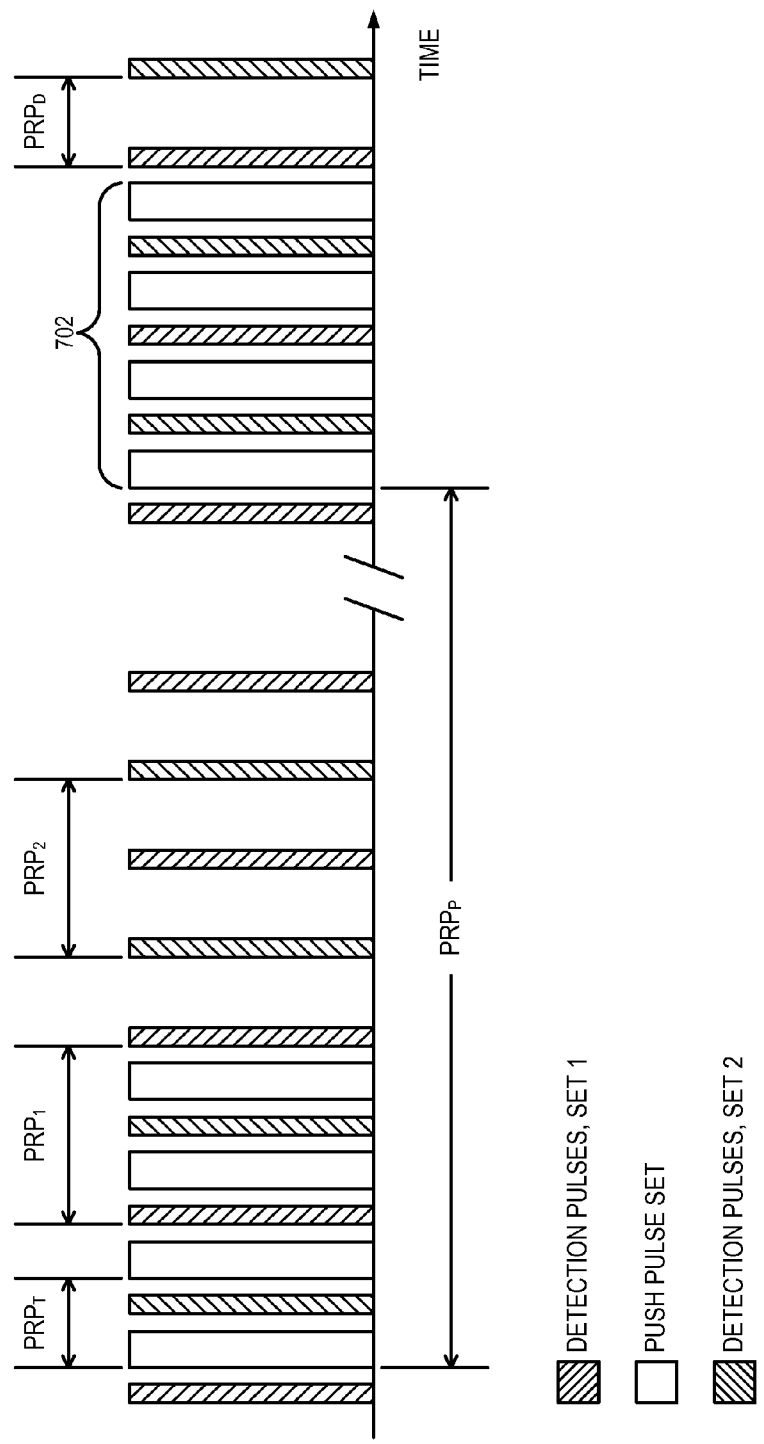
FIG. 7 is another pulse timing diagram indicating the application of a set of short ultrasonic vibration tone bursts and ultrasonic detection pulses in accordance with the present invention, and in which the detection pulses are applied to more than one detection point.
Figure 8:
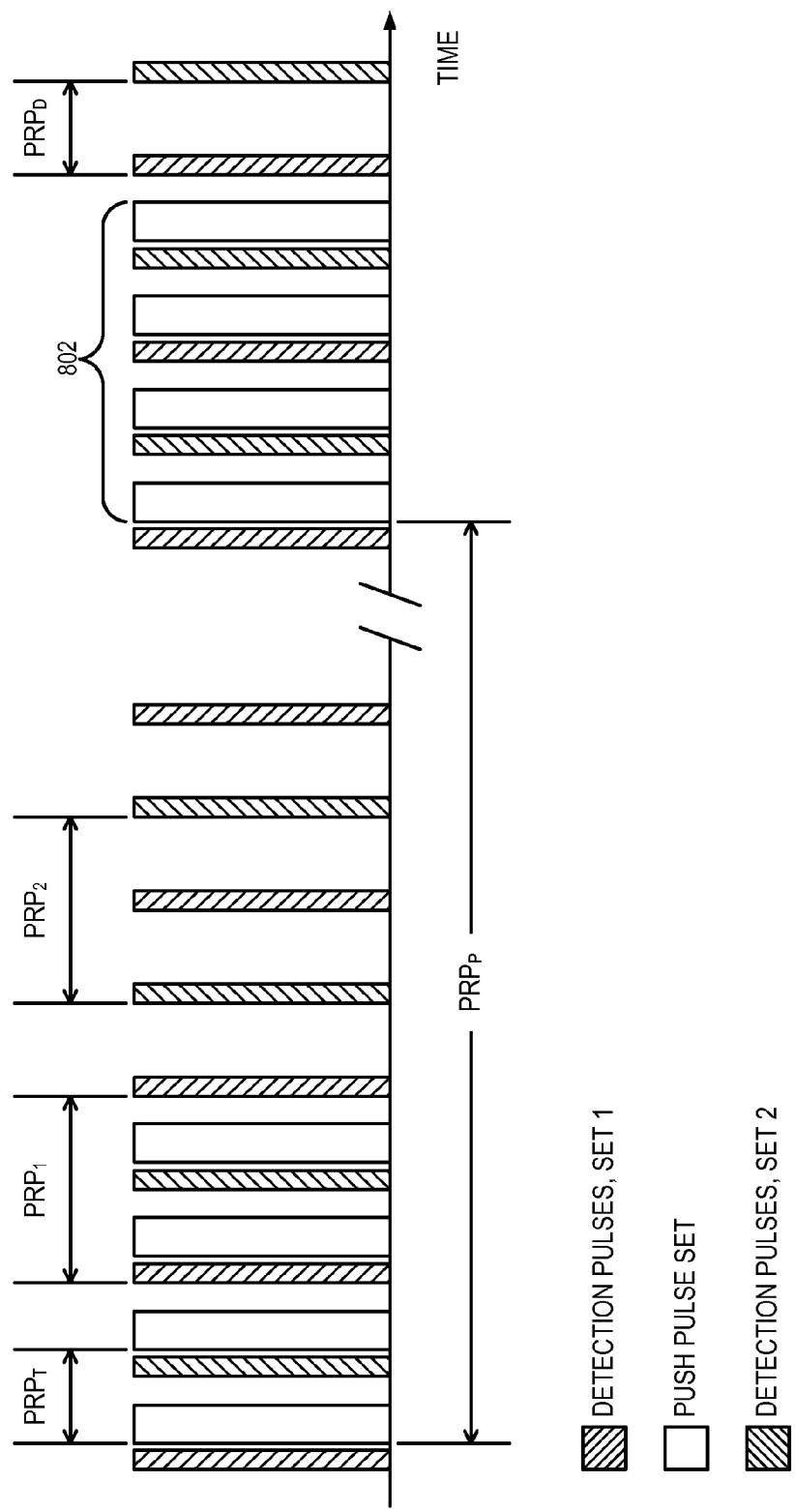
FIG. 8 is yet another pulse timing diagram indicating the application of a set of short ultrasonic vibration tone bursts and ultrasonic detection pulses in accordance with the present invention, and in which the detection pulses are applied to more than one detection point.

Referring now to FIG. 7, an exemplary temporal pulse sequence in which a set of ultrasonic vibration pulses is interleaved with a series of motion detection pulses is shown. More particularly, two sets of detection pulses are implemented: a first set directed at a first detection point, and a second set directed at a second detection point. While any given detection pulse is repeated at a pulse repetition frequency, $PRF_D$, which is still equal to the pulse repetition frequency of the vibration tone bursts, $PRF_T$, the pulse repetition frequency between detection pulses of the same set is identified as $PRF_1$ for the first set, and as $PRF_2$ for the second set. In general, $PRF_1=PRF_2=PRF_D/2$.

Using this pulsing scheme, motion curves at both the first and second motion detection points are obtained all at once. Acquiring measurements at only two locations is sufficient for SDUV analysis; however, using this pulse sequence, detection at the first and second locations will have a delay of ¼ kHz=0.25 ms, which will need to be accounted for when calculating phase delay at these two locations for shear wave speed estimation.

The vibration tone bursts can be moved up earlier in time as shown in FIG. 8. This modification increases the time interval between each vibration tone burst and its subsequent detect beam, which reduces the interference of the vibration tone burst with motion detection. For example, the vibration tone burst can be moved up to a time point just after the pulse-echo of the previous detect beam is finished; that is, when echoes from the desired tissue of interest reach the transducer and are stored.

Sequential detection can also be implemented. In sequential detection, the detect beams, such as those shown in FIG. 6, are directed to the same detection location for a number of push cycles before moving to the next detection location. For example, detection at each location is done for two push cycles. In general, a longer detection duration will improve signal-to-noise ratio ("SNR"). By way of example, if each push cycle is around ten milliseconds in duration (five millisecond push duration and five millisecond duration with no pushing), then the detection at, for example, five different motion detection locations would account for a push cycle duration of twenty milliseconds at each location with a PRF of 4 kHz. Thus, in a total of 100 milliseconds for ten push cycles, motion at five different locations along the shear wave propagation path can be obtained and used for SDUV analysis.

The net ultrasound push time can be increased to increase tissue motion for more reliable detection. This is achieved by increasing the duration of each vibration tone burst or by increasing the number of vibration tone bursts in each set of tone bursts. The pulse repetition frequency of the pulse sequence should be adjusted accordingly to avoid interference and allow sufficient time for the tissue to recover after each push. In addition, moving the short tone bursts up in time, as illustrated in FIG. 8, can be applied to all approaches to minimize interference from pushing.

While the foregoing pulse sequences describe situations in which one ultrasonic vibration tone burst is interleaved between successive ones of the motion detection pulses, other variations are possible. For example, two or more vibration tone bursts can be applied between successive ones of the motion detection pulses. Similarly, more than one motion detection pulse can be applied between successive ones of the ultrasonic vibration tone bursts in the set of ultrasonic vibration tone bursts.

Figure 9:
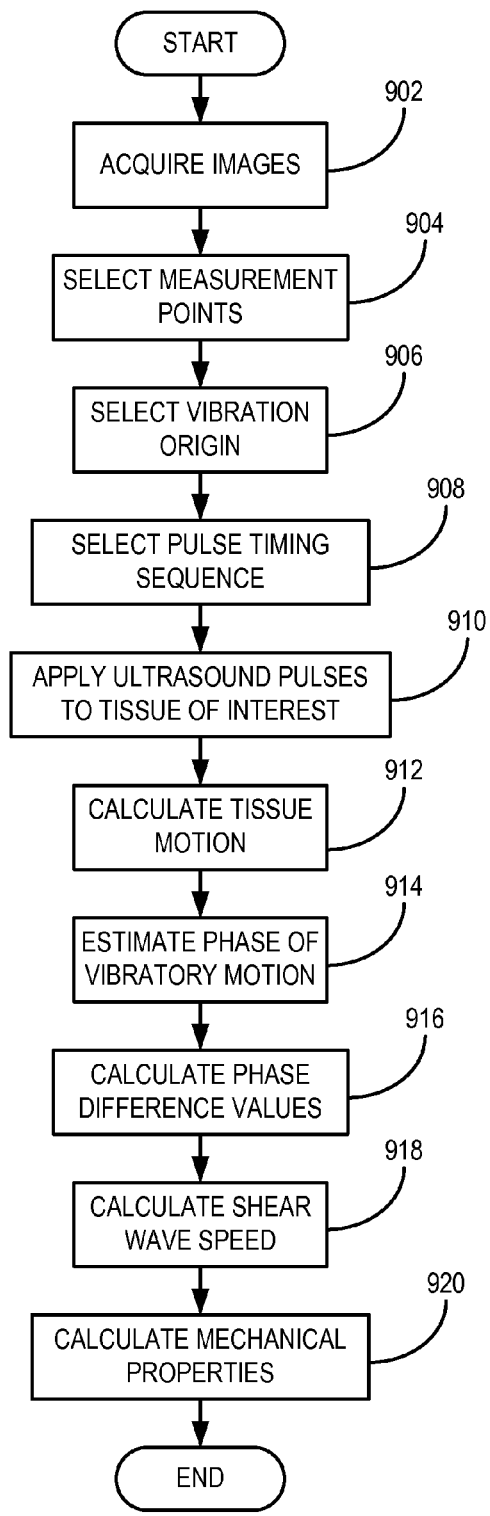
FIG. 9 is a flow chart setting forth the steps of a method for measuring the mechanical properties of a tissue of interest in accordance with the present invention.

Referring particularly now to FIG. 9, a flowchart setting forth the steps of an exemplary method for measuring mechanical properties, such as shear elasticity and shear viscosity, of a tissue of interest using a shear wave speed dispersion technique is illustrated. This method is performed with an ultrasound system 200, such as the one described above. The mechanical property processor 528 controls the measurements made by the ultrasound system 200, the vibration pulse output of the transducer elements 304, processes the resulting echo signals I and Q and calculates a mechanical property of the target tissues. Such target tissues may be, for example, a liver, a breast, an artery, or myocardial tissue, and the mechanical property may be stiffness or viscosity.

The ultrasound system 200 is, for example, operated first using B-mode scanning to acquire an anatomical ultrasound image of a region of interest, such as the heart or liver, as indicated at step 902. Next, a target of interest is determined such as by selecting in the ultrasound image a plurality of measurement points at which it is desired to obtain mechanical properties, as indicated at step 904. Then, at process block 906, a vibration origin is selected. The vibration origin and the plurality of motion detection points are, for example, selected to be co-linear and spaced as discussed below. These selections can be provided to the ultrasound system in a variety of ways, such as, for example, by entering data, using a display to select among options, or using a touch screen or selector on an ultrasound image screen.

As previously described herein, the shear wave speed dispersion technique makes use of an estimation of wave speed, which includes a phase difference, such that the phase, $\phi_s$, of the echo signals is determined at a plurality of points. This is achieved, for example, using a single vibration origin and two or more different motion detection points, each located a different distance from the vibration origin. However, it is also possible to use a single detection point and to change the vibration origin position.

The determination of a desired distance, R, between a vibration origin and a motion detection point and the determination of a desired spacing, $\Delta r$, between the motion detection points can be based on a consideration of the type of tissue that is under examination. For example, an appropriate distance, R, in the liver may be on the order of one centimeter, while an appropriate distance, R, for a breast lesion may be on the order of five millimeters. The outgoing shear wave generated at the vibration origin can be approximated as a cylindrical shear wave. Its amplitude decreases as the wave propagates outwards from the excitation center due to both geometry effects and attenuation resulting from the medium in which the wave propagates. Therefore, it is desirable to have the detection points close to the vibration origin to get higher vibration amplitude. On the other hand, locations too close to the vibration origin will be subject to the near field effect and thus the phase of the shear wave will deviate from a linear relationship with the traveled distance. This near field effect increases for stiffer tissue. However, $\Delta r$ cannot be too large, otherwise the vibration amplitude will be too small for reliable phase estimation. Therefore, the precision of shear wave dispersion characterization can be improved by optimizing the position and range of vibration detections, which may be dependent on the type of tissue under evaluation, and by increasing the vibration amplitude as discussed above.

Referring still to FIG. 9, after the vibration origin and motion detection points have been selected, the desired pulse sequence used to drive the vibration and detection modes of the ultrasound system are selected, as indicated at step 908. For example, one of the pulse sequences illustrated in FIGS. 6-8 is selected. Next, the transmission of intermittent sets of ultrasonic vibration tone bursts to a vibration origin, and the transmission of ultrasonic detection pulses and the receipt of echo signals from the motion detection point occurs under the control of the digital controller 312 of the ultrasound system 200, as indicated at step 910. The sets of ultrasonic vibration tone bursts are applied to the subject in an interleaved time sequence with a detection mode occurring during the off intervals of each vibration tone burst. As described above, the push cycle is repeated multiple times at a push pulse repetition frequency, $PRF_P$. In some instances, only one push cycle may be applied. In these instances, a transient shear wave containing multiple frequency components will be generated.

The ultrasound system 200 is operated to acquire echo signals from the subject tissues at a series of motion detection points. The ultrasonic detection pulses can be applied to the motion detection points in a number of ways. For example, each motion detection point can be fully sampled before the detection pulses are steered to the next point. However, in the alternative, the plurality of motion detection points can be sampled substantially contemporaneously, as described above. In one configuration, parallel beamforming is employed in both the transmission of the detection pulses and the reception of the resulting echo signals. In general, a substantially plane wave is produced in the region of the tissue of interest undergoing harmonic shear wave motion by properly phasing the transducer elements 304. This results in a rather broad beam instead of a focused ultrasound beam. The backscattered ultrasound is then formed into focused beams in a beamformer after being received by the transducer 302. In another configuration, the transducer elements 304 are energized in subgroups such that a plurality of focused ultrasound beams are directed to the plurality of motion detection points.

Referring again to FIG. 9, tissue motion is calculated from ultrasound echoes received from the detection pulses, as indicated at step 912. One exemplary method used to calculate this tissue motion is I-Q demodulation, as explained above by Eqn. (7). Alternatively, tissue motion can also be obtained by correlation of ultrasound echoes. In yet another example, tissue motion can be estimated by processing ultrasound echoes in the frequency domain, such as is described by H. Hasegawa and H. Kanai, in "Improving Accuracy in Estimation of Artery-Wall Displacement by Referring to Center Frequency of RF Echo," *IEEE Trans. Ultrasonics, Ferroelectrics, and Frequency Control*, 2006; 53(1):52-63.

As indicated at process block 914, the amplitude and phase of the shear wave at each point is then estimated from the tissue motion information acquired in step 912. As described above, there are a number of different methods for accomplishing this, and the method outlined in Eqns. (10)-(13) is just one example. Kalman filtering, as indicated by Eqns. (20) and (21) is another option. In addition, amplitude and phase values of the shear wave can also be estimated in the frequency domain by performing a Fourier transform on the time-domain tissue displacement signal and examining the frequency components of the multi-tone shear wave (e.g., at 100, 200, 300, 400, and 500 Hz). In yet another example, correlation of the time-domain tissue displacement signals with a sine signal of the same frequency (e.g., 100, 200, 300, 400, or 500 Hz) can be used to estimate phase of the signal at that frequency.

As indicated by process block 916, the change in tissue oscillation phase as a function of distance is then calculated for the vibration frequency and its harmonics using the calculated phase values at the corresponding motion detection points. For example, shear wave speeds are calculated at the frequencies including 100 Hz, 200 Hz, 300 Hz, 400 Hz and 500 Hz.

As indicated at process block 918, the next step is to calculate the shear wave speeds in the subject tissue 206 at the different vibration frequencies. Linear regression is applied to the phase changed measurements to yield a phase change over the selected distance in the tissue of interest. From this phase change over distance information, the shear wave speed at each vibration frequency is estimated by Eqn. (22).

As indicated at process block 920, a mechanical property of the tissue 206 is then calculated from the shear wave speed information. For example, the stiffness and viscosity of the tissue 206 are estimated from the set of shear wave speeds. These mechanical properties indicate the stiffness of the tissue of interest, which is a valuable clinical measurement. This calculation is based on shear wave speed dispersion as described, for example, by S. Chen, et al., in "Complex Stiffness Quantification Using Ultrasound Stimulated Vibrometry," *IEEE Ultrasonics Symposium*, 2003; 941-944. The shear wave speeds at multiple frequencies are fit with appropriate theoretical models to solve for the shear elasticity and viscosity. For example, one appropriate equation is the so-called Voigt model:

$$c_s = \sqrt{\frac{2(\mu_1^2 + \omega^2 \mu_2^2)}{\rho(\mu_1 + \sqrt{\mu_1^2 + \omega^2 \mu_2^2})}};$$  Eqn. (24)

where $c_s$ is the shear wave speed, $\mu_1$ is the shear modulus, $\mu_2$ is the shear viscosity, $\omega$ is frequency, and $\rho$ is the density of the tissue, which can be assumed to be 1000 kilograms per cubic meter (kg/m₃).

While the analysis of the received echo signal is performed in the mid-processor section of an ultrasound receiver in the method described above, it should be apparent that these functions can similarly be performed in a separate processor or computer workstation.

Thus, in general, vibratory motion is detected at a motion detection point by transmitting detection pulses to the motion detection point and receiving echo pulses therefrom. These signals are then analyzed as described above in the mid-processor 502 of the receiver 308. A signal indicative of the induced harmonic shear wave motion is detected at the prescribed frequency and its harmonics in the received ultrasonic echo signals and a characteristic of the detected signal, such as amplitude or phase, is determined. The mechanical property is then calculated using the measured characteristic. Depending on the model used to relate a measured characteristic to a mechanical property, it may be necessary to determine a measured characteristic at more than one point or at more than one frequency. For example, using the Voigt dispersion model requires shear wave speeds to be calculated at a plurality of frequencies. Using Eqn. (22) to calculate the shear wave speed, $c_s$, requires phase measurements at two or more motion detection points.

In other embodiments, rather than measuring a phase difference and using the Voigt model, an amplitude could be measured and the change in amplitude over distance could be determined and used in conjunction with an appropriate model to determine one or more other mechanical properties of the subject target tissue. For example, the shear wave amplitude at the vibration frequency (e.g., 100 Hz) obtained at several locations along its propagation path can be used to estimate the shear wave attenuation, α, at that frequency. A diffraction effect, in which the wave spreads over a larger surface as it propagates, can also cause a decrease in the wave amplitude as the shear wave propagates outwards from the push origin; therefore, this effect should be accounted for to calculate α correctly. By way of example, the diffraction effect can be estimated by computer simulation. For example, the three-dimensional intensity field of the transducer can be simulated by Field II ultrasound simulation software, as described by J. A. Jensen in "Field: A Program for Simulating Ultrasound Systems," *Paper presented at the 10th Nordic-Baltic Conference on Biomedical Imaging Published in Medical & Biological Engineering & Computing*, pp. 351-353, Volume 34, Supplement 1, Part 1, 1996; and by J. A. Jensen and N. B. Svendsen in "Calculation of Pressure Fields from Arbitrarily Shaped, Apodized, and Excited Ultrasound Transducers," *IEEE Trans. Ultrason., Ferroelec., Freq. Contr.*, 39, pp. 262-267, 1992. This three-dimensional intensity field may then used to estimate the force field of the push beam, which then can be used with Finite Element Method or Green's function simulation to calculate wave attenuation due to diffraction effects in a pure elastic medium. The shear modulus of the medium required for these simulations can be estimated from the measured shear wave speed:

$$\mu_1 = \rho \cdot c_s^2 \qquad (25).$$

Shear wave attenuation, α, and speed, $c_s$, at the same frequency can then be used to estimate tissue shear modulus $\mu_1$, and shear viscosity $\mu_2$ with the Voigt model:

$$\mu_1 = \frac{\rho c_s^2 \omega^2 (\omega^2 - \alpha^2 c_s^2)}{(\omega^2 + \alpha^2 c_s^2)^2};$$  Eqn. (26)

and

-continued $$\mu_2 = \frac{2\rho c_s^3 \omega^2 \alpha}{(\omega^2 + \alpha^2 c_s^2)^2};$$ Eqn. (27)

where ω is frequency and ρ is the density of the tissue, which can be assumed to be 1000 kilograms per cubic meter (kg/m$_3$). The shear wave speed, $c_s$, can be obtained from the phase measurements as described above. In contrast to Eqn. (24), measurements are needed at only one frequency to calculate $\mu_1$ and $\mu_2$ using Eqns. (26) and (27). Typically, the vibration frequency is processed because tissue motion at the vibration frequency (e.g., 100 Hz) is usually much higher than that at its harmonics (e.g., 200, 300, 400 Hz). Therefore, it is contemplated that the approach employing Eqns. (26) and (27) is more robust in the presence of noise compared to the approach employing Eqn. (24).

The present invention has been described in terms of one or more preferred embodiments, and it should be appreciated that many equivalents, alternatives, variations, and modifications, aside from those expressly stated, are possible and within the scope of the invention.

The invention claimed is:

1. A method for measuring a mechanical property of a subject with an ultrasound system, the steps of the method comprising:
   a) producing a shear wave that propagates outward from a vibration origin in the subject by applying to the vibration origin with an ultrasonic transducer during each of a plurality of successive push cycles, a set of ultrasonic push pulses comprising a plurality of ultrasonic push pulses spaced apart in time by a push pulse repetition period with each push pulse set being spaced apart in time by a push pulse set repetition period that is longer than the push pulse repetition period;
   b) acquiring echo signal data from at least two motion detection points in the subject by applying to the at least two motion detection points with the ultrasonic transducer, a plurality of ultrasonic detection pulses spaced apart in time by a detection pulse repetition period;
   c) detecting a signal indicative of the shear wave produced in step a) by analyzing the echo signal data acquired in step b);
   d) determining at least one of a phase and an amplitude of the signal detected in step c);
   e) calculating a mechanical property of the subject using the at least one of a phase and an amplitude determined in step d);
   wherein successive ones of the plurality of ultrasonic detection pulses are interleaved in time with successive ones of the plurality of ultrasonic push pulses; and
   wherein at least two of the plurality of ultrasonic push pulses are applied between successive ones of the plurality of ultrasonic detection pulses.

2. The method as recited in claim 1 in which each of the plurality of ultrasonic detection pulses is directed to a different one of the at least two motion detection points.

3. The method as recited in claim 1 in which the plurality of ultrasonic push pulses and the plurality of ultrasonic detection pulses are interleaved in time such that each of the plurality of ultrasonic push pulses is applied closer in time to a preceding ultrasonic detection pulse than to a succeeding ultrasonic detection pulse.

4. The method as recited in claim 1 in which the plurality of ultrasonic push pulses are applied in step a) in a series of successive push cycles, and in which the plurality of ultrasonic detection pulses are applied to the at least two motion detection points in step b) at least once during each push cycle of the series of successive push cycles.

5. The method as recited in claim 4 in which each of the plurality of ultrasonic detection pulses is applied to a different one of the at least two motion detection points such that at least one ultrasonic detection pulse is applied to each of the at least two motion detection points during each push cycle in the series of successive push cycles.

6. The method as recited in claim 1 in which the plurality of ultrasonic push pulses produce a shear wave at a prescribed frequency and harmonics thereof, and the signal detected c) is indicative of the shear wave at the prescribed frequency and harmonics thereof.

7. The method as recited in claim 1 in which the plurality of ultrasonic push pulses are ultrasonic tone bursts.

8. The method as recited in claim 1 in which step d) includes determining an amplitude of the signal detected in step c), and correcting the determined amplitude for diffraction effects.

9. The method as recited in claim 8 in which the determined amplitude is corrected for diffraction effects in step d) by estimating a force field produced by the plurality of ultrasonic push pulses and estimating a wave attenuation from the estimated force field.

10. A method for measuring a mechanical property of a subject with an ultrasound system, the steps of the method comprising:
    a) producing a shear wave that propagates outward from a vibration origin in the subject by applying to the vibration origin with an ultrasonic transducer during each of a plurality of successive push cycles, a set of ultrasonic push pulses comprising a plurality of ultrasonic push pulses spaced apart in time by a push pulse repetition period with each push pulse set being spaced apart in time by a push pulse set repetition period that is longer than the push pulse repetition period;
    b) acquiring echo signal data from at least two motion detection points in the subject by applying to the at least two motion detection points with the ultrasonic transducer, a plurality of ultrasonic detection pulses spaced apart in time by a detection pulse repetition period;
    c) detecting a signal indicative of the shear wave produced in step a) by analyzing the echo signal data acquired in step b);
    d) determining at least one of a phase and an amplitude of the signal detected in step c);
    e) calculating a mechanical property of the subject using the at least one of a phase and an amplitude determined in step d);
    wherein successive ones of the plurality of ultrasonic detection pulses are interleaved in time with successive ones of the plurality of ultrasonic push pulses; and
    wherein the plurality of ultrasonic push pulses and the plurality of ultrasonic detection pulses are interleaved in time such that an equal duration of time exists between each successive ultrasonic pulse.

11. The method as recited in claim 10 in which at least two of the plurality of ultrasonic detection pulses are applied between successive ones of the plurality of ultrasonic push pulses.

12. The method as recited in claim 10 in which the plurality of ultrasonic push pulses are applied in step a) in a series of successive push cycles, and in which the plurality of ultrasonic detection pulses are applied to the at least two motion detection points in step b) at least once during each push cycle of the series of successive push cycles.

13. The method as recited in claim 12 in which each of the plurality of ultrasonic detection pulses is applied to a different one of the at least two motion detection points such that at least one ultrasonic detection pulse is applied to each of the at least two motion detection points during each push cycle in the series of successive push cycles.

14. The method as recited in claim 10 in which the plurality of ultrasonic detection pulses are grouped into two subsets of ultrasonic detection pulses that are interleaved in time, and in which ultrasonic detection pulses in each of the two subsets are spaced apart in time by a subset detection pulse repetition period that is greater than the detection pulse repetition period of the plurality of ultrasonic detection pulses.

15. The method as recited in claim 10 in which the plurality of ultrasonic push pulses are ultrasonic tone bursts.

16. A method for measuring a mechanical property of a subject with an ultrasound system, the steps of the method comprising:
   a) producing a shear wave that propagates outward from a vibration origin in the subject by applying to the vibration origin with an ultrasonic transducer during each of a plurality of successive push cycles, a set of ultrasonic push pulses comprising a plurality of ultrasonic push pulses spaced apart in time by a push pulse repetition period with each push pulse set being spaced apart in time by a push pulse set repetition period that is longer than the push pulse repetition period;
   b) acquiring echo signal data from at least two motion detection points in the subject by applying to the at least two motion detection points with the ultrasonic transducer, a plurality of ultrasonic detection pulses spaced apart in time by a detection pulse repetition period;
   c) detecting a signal indicative of the shear wave produced in step a) by analyzing the echo signal data acquired in step b);
   d) determining at least one of a phase and an amplitude of the signal detected in step c);
   e) calculating a mechanical property of the subject using the at least one of a phase and an amplitude determined in step d);
   wherein successive ones of the plurality of ultrasonic detection pulses are interleaved in time with successive ones of the plurality of ultrasonic push pulses; and
   wherein the push pulse repetition period and the detection pulse repetition period are equal.

17. The method as recited in claim 16 in which the plurality of ultrasonic push pulses and the plurality of ultrasonic detection pulses are interleaved in time such that each of the plurality of ultrasonic push pulses is applied closer in time to a preceding ultrasonic detection pulse than to a succeeding ultrasonic detection pulse.

18. The method as recited in claim 16 in which the plurality of ultrasonic push pulses are applied in step a) in a series of successive push cycles, and in which the plurality of ultrasonic detection pulses are applied to the at least two motion detection points in step b) at least once during each push cycle of the series of successive push cycles.

19. The method as recited in claim 18 in which each of the plurality of ultrasonic detection pulses is applied to a different one of the at least two motion detection points such that at least one ultrasonic detection pulse is applied to each of the at least two motion detection points during each push cycle in the series of successive push cycles.

20. The method as recited in claim 16 in which the plurality of ultrasonic push pulses are ultrasonic tone bursts.

* * * * *